US00PP35141P2

(12) United States Plant Patent
Hansen

(10) Patent No.: US PP35,141 P2
(45) Date of Patent: Apr. 25, 2023

(54) ***ECHINACEA* PLANT NAMED 'THE FUCHSIA IS BRIGHT'**

(50) Latin Name: ***Echinacea* hybrid**
Varietal Denomination: The Fuchsia Is Bright

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,771

(22) Filed: Nov. 16, 2022

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

*Primary Examiner* — Kent L Bell

(57) ABSTRACT

The new and distinct cultivar of *Echinacea* plant named 'The Fuchsia is Bright' with large fragrant inflorescences on strong, branched stems producing single whorls of bright fuchsia-pink colored, overlapping, ray florets on dark reddish stems. The large inflorescence produces ray florets that tend to stay nearly horizontal through maturity. The new plant flowers from mid-summer to late summer, and is suitable as a potted plant, for the landscape, and for cut flower arrangements.

1 Drawing Sheet

Botanical denomination: *Echinacea* hybrid.
Cultivar designation: 'The Fuchsia Is Bright'.

STATEMENT REGARDING PRIOR DISCLOSURES UNDER 37 CFR 1.77(b)(6)

The first non-enabling disclosures of the claimed plant, in the form of a photograph and brief description was on a website operated by Walters Gardens, Inc. on Dec. 1, 2021, followed by a photograph and brief description in the "Walters Gardens 2022-2023 Catalog" on Jun. 8, 2022. The claimed plant was first sold on Aug. 1, 2022, to Garden Crossings and to W.W. Greenhouses by Walters Gardens, Inc., who obtained the plant and all information relating thereto, from the inventor. No plants of *Echinacea* 'The Fuchsia Is Bright' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'The Fuchsia Is Bright'. The new plant was the result of a cross by the inventor of an unnamed proprietary hybrid known as 15-11-2 (not patented) as the female parent and an unnamed proprietary hybrid known as 15-6-2 (not patented) as the male parent on Aug. 8, 2016, at a wholesale perennial nursery in Zeeland, Mich. The single seedling selected was evaluated initially in trials in the summer of 2017 at the same nursery and assigned the breeder code of 16-98-1.

*Echinacea* 'The Fuchsia Is Bright' has been asexually propagated at the same nursery by crown division and also using careful shoot tip tissue culture procedures and found to reproduce plants that exhibit all the characteristics identical to the original plant in successive generations.

*Echinacea* 'The Fuchsia Is Bright' is distinct from all other Coneflowers known to the inventor. The nearest comparison cultivars are: 'Delicious Candy' (not patented), 'PowWow Wild Berry' U.S. Pat. No. 7,982,110, 'Merlot' U.S. Plant Pat. No. 18,814, 'Ruby Giant' (not patented), 'Coral Craze' U.S. Plant Pat. No. 31,889, and 'Mystic' (not patented).

The female parent plant, 15-11-2, has smaller inflorescences with pink ray florets on more compact habit. The male parent plant, 15-6-2, has larger inflorescences with orange ray florets with less ligule overlapping and less basal branching.

'Delicious Candy' has a smaller inflorescence with ray florets of a darker raspberry-red that are shorter and disk florets that are much larger producing a pompon disk. 'PowWow Wild Berry; has smaller inflorescences with ray florets that are shorter and deeper purplish-pink to magenta colored. 'Merlot' has a much taller habit with broader and shorter inflorescences that have more numerous ray florets of a darker purplish-red. 'Ruby Giant' is taller and has a double row of ray florets that are lighter reddish-purple in color. 'Coral Craze' has slightly larger inflorescences and the color is a deeper and more intense rose on slightly taller plants. 'Mystic' is smaller in habit, has smaller inflorescences that have shorter ray florets of a more orangish-red color that fade significantly to a light coral pink.

SUMMARY OF THE INVENTION

*Echinacea* 'The Fuchsia Is Bright' has not been evaluated under all possible environmental conditions. The phenotype may vary with variations in environment including: growing temperature, available sunlight, nutrients, water, etc. without a change in the genotype of the plant. The new plant is distinct from its parents and all other *Echinacea* known to the applicant in the following combined traits:

1. Fragrant inflorescences on strong branched stems;
2. Large, broad inflorescences with dark reddish stems;
3. single whorl of ray florets that tend to stay nearly horizontal in inflorescence maturity;
4. Ray florets of bright fuchsia-pink coloration;
5. Vigorous growth and excellent habit;
6. Dark-green narrowly ovate foliage.

BRIEF DESCRIPTION OF THE DRAWINGS

The photographs of 'The Fuchsia Is Bright' demonstrate the overall appearance of the plant including the unique traits. The drawings of the new plant are of a two-year-old plant grown in a full-sun trial garden in Zeeland, Mich. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
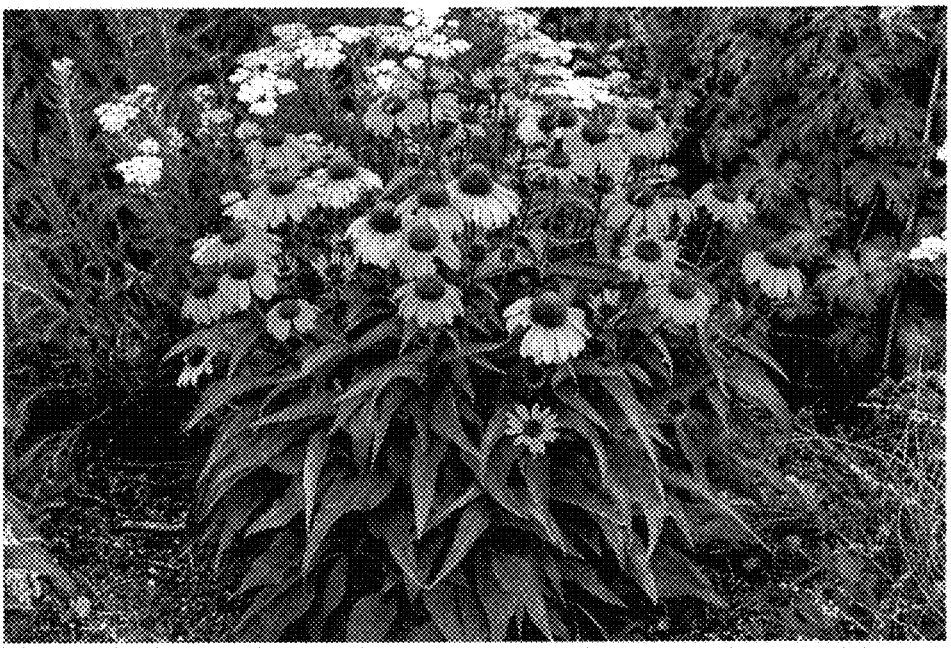
FIG. 1 shows the habit of the new plant in flower.
Figure 2:
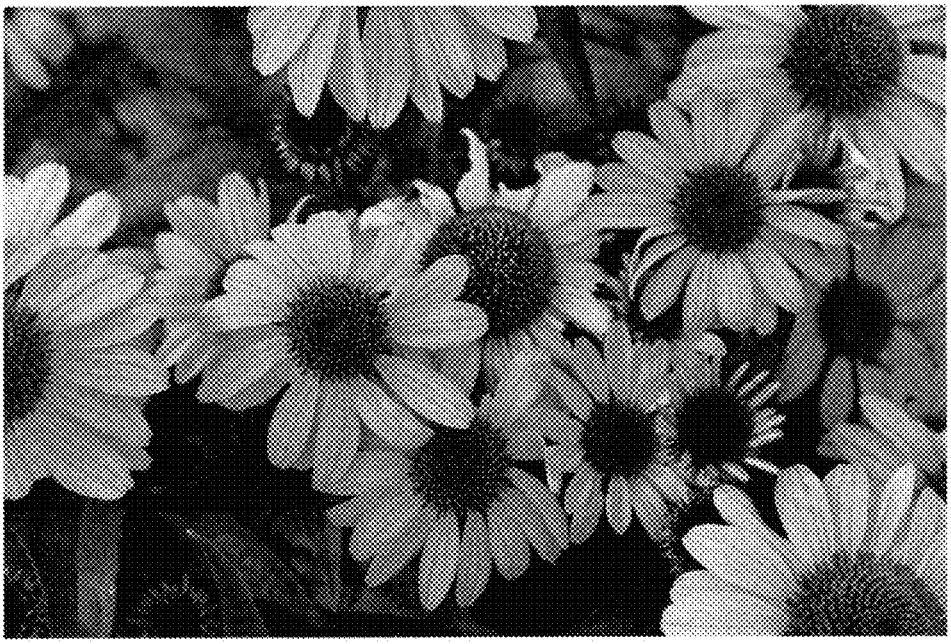
FIG. 2 shows a close up of some inflorescences from above.

The following description of *Echinacea* 'The Fuchsia Is Bright' is based on observations of two-year-old specimens grown in a partially-shaded greenhouse and in a full-sun trial garden in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is the proprietary unreleased hybrid 15-11-2 comprising a complex cross with 'Julia' U.S. Plant Pat. No. 24,629 and 'Butterfly Kisses' U.S. Plant Pat. No. 24,458, and the male parent is the proprietary unreleased hybrid 15-6-2 comprising a complex crossing with offspring from 'Julia', 'Cleopatra' U.S. Plant Pat. No. 24,631 and Butterfly Kisses' U.S. Plant Pat. No. 24,458;

Plant habit: Multi-stemmed, freely-branched, hardy herbaceous perennial, flowering to about 40 cm tall and 38 cm wide with foliage to 22 cm tall and 35 cm wide;

Growth rate: Vigorous, finishing in 4-liter containers in about 2 months during the summer;

Roots: Cream-colored, finely branched;

Foliage: Alternate; narrowly ovate; acute apex; cuneate to attenuate base; margin micro-ciliolate and serrate to serrulate with teeth to about 3 mm long and 5 mm wide; hirsutulous abaxial and adaxial; to about 13.8 cm long and 6.3 cm wide decreasing distally, average about 10 cm long and 4 cm wide;

Leaf color: Young leaves adaxial between RHS146A and RHS 138A, abaxial nearest RHS 147B; mature leaves adaxial between NN137A and RHS 139A, abaxial nearest RHS 137B; variegation absent;

Foliage fragrance: Lightly herbal;

Venation: Pinnate; abaxial midrib and veins costate; glabrous adaxial, hirsutulous abaxial;

Vein color: Adaxial midrib and primary veins nearest RHS 146D, secondary nearest RHS 146A; abaxial midrib and primary veins nearest RHS 146D, secondary nearest RHS 146A;

Petiole: Concavo-convex; glabrous adaxial; and finely hirsutulous abaxial; to about 8 cm long and 4 mm wide at the base on lowest leaves and decreasing to nearly sessile distally;

Petiole color: Adaxial center nearest 145C and margin between RHS146A and RHS 138A, abaxial center between RHS 146D and RHS 145C and margin nearest RHS 137B;

Stem: Hirsutulous; cylindrical, fistulous; strong and stiff; to about 37 cm long including peduncle and about 6 mm diameter at base; average 35 cm long and 5 mm diameter;

Stem color: Proximally nearest RHS 146C and distally blushed to solid RHS 183B;

Peduncle: Hirsutulous; terete; strong; stiff; branched; about 11 cm long above last leaves and 3 mm diameter at base; quantity per plant about 12; aspect ascending, upright;

Peduncle color: Proximally between RHS 146C and RHS 183B, distally to solid RHS 183B;

Internode: 6 to 9 per stem; average about 5.6 cm long, shorter proximally and longer distally; node color same as surrounding peduncle;

Branches: Cylindrical; hirsutulous; tightly angled to main stem to about 60° above horizontal: about 2 to 4 branches per stem; to about 18 cm long and 2.5 mm diameter;

Branch color: Proximally between RHS 146C and RHS 183B, distally to solid RHS 183B;

Inflorescence: Bracteate head, aggregate of achene; with single whorl of distinct ligulate ray florets and disk florets in a pappus; flowering mid-summer to late summer; initial inflorescence largest, to about 10.5 cm wide and 5.5 cm tall, with cones 2.8 cm across and 2.7 cm tall; to 4 inflorescences per peduncle;

Inflorescence fragrance: Lightly sweet, honey-like;

Flower persistence: Remaining effective in color for 10 to 14 days depending on temperatures, cone drying on plant and effective into winter;

Involucre: With numerous bracts, about 40 per inflorescence in 3 to 4 whorls; arcuate downward toward peduncle;

Involucre bracts: Lanceolate; narrowly acute apex; truncate base; micro-ciliolate margin; adaxial glabrous to micro-puberulent; abaxial hirsutulous; to about 11 mm long and 3.5 mm across decreasing distally; color adaxial center between RHS 137A and RHS 137B, abaxial nearest RHS 147B with a light blush of nearest RHS 186A;

Inflorescence buds with ray florets vertical and still enrolled: About 14 mm across and 20 mm tall; ray floret color between RHS N77A and RHS N186D with spines nearest RHS 187A;

Ray florets: Zygomorphic; arrangement in single whorl, frequently moderately imbricate; ligulate; apex emarginated with two notches to 2 mm deep; base attenuate; margin entire; adaxial and abaxial surfaces matte; 16 to 26 per inflorescence; opening to horizontal, drooping up to only 20 degrees below horizontal with maturity; flat, twisting absent; sterile; ray floret to 42 mm long and 12 mm wide near middle, base 2 mm wide; average size 38 mm long, 11 mm wide at center tapering to 2 mm wide at base; adaxial veins thickened and raised;

Ray floret color: Changing with maturity; when first horizontal young adaxial nearest RHS 71B lightening to between RHS 64B to RHS 64C in mid-open period and between RHS N155C and RHS N170D before dropping, basal 3 to 4 mm remaining constant between RHS 146A and RHS 146D in both adaxial and abaxial; abaxial beginning nearest RHS 70B when first horizontal, becoming between RHS 186D and 170D in mid-open period and between RHS 159C and RHS N170D before dropping;

Disk florets: About 300 per head; actinomorphic; perfect; synandrous; produced in raised dome, about 2.8 cm across and 2.7 cm tall;

*Disk floret corolla*.—Fused forming tube; about 9 mm long and 3 mm wide, fused in tube in basal 8 mm, free in distal 1 mm; individual disk florets about 0.5 mm wide at fusion; acute apex; entire margin; both surfaces slightly lustrous.

*Disk floret corolla tube color*.—Adaxial and abaxial nearest RHS 146D with apex nearest RHS N186C.

*Disk floret androecium*.—Five; synandrous.

*Androecium*.—Present on disk florets only.

*Staminal column*.—About 0.7 mm wide and protrudes from corolla tube about 2 mm; five fused stamens; color between RHS N199B and RHS 199B.

*Anthers*.—Fused, about 2.5 mm long and 0.7 mm diameter; color between RHS N199B and RHS 199B.

*Filaments*.—Five; attached to column; thin, less than 0.2 mm diameter and 2 mm long; color nearest RHS NN155B.

*Pollen*.—Abundant; globose; less 0.1 mm in diameter; color nearest RHS 14A.

*Gynoecium*.—On disk florets only; single; to 10 mm long.

*Style*.—About 4 mm long and 0.2 mm diameter; color nearest RHS 187B.

*Stigma*.—Bifid; about 1.5 mm long and 0.3 mm diameter; color nearest RHS 187A.

*Fruit*.—Has not yet been observed.

Receptacle spines: With disk florets; acicular; glabrous; lustrous; to 11 mm long and 2 mm across near middle;

Spine color: With ray florets first horizontal apices nearest RHS 187A, center portion nearest 28A, and bases nearest RHS NN155C; mature flower apices nearest RHS 183A, central portion nearest RHS N172A, and base nearest RHS 151D; after ray florets fall apices between RHS N172A and RHS 173A, midsection nearest RHS 138A with base nearest RHS 145D; after dried base nearest RHS N200A and distal 5.0 mm nearest RHS 202A;

Disease and pest resistance: Resistance and susceptibility beyond that of other hardy Coneflower cultivars have not been observed.

Growth: The plant grows best with plenty of moisture and adequate drainage but is able to tolerate some drought when mature.

Winter hardiness: At least from USDA zone 4 through 8.

I claim:

1. A new and distinct cultivar of *Echinacea* plant named 'The Fuchsia is Bright' as herein described and illustrated.

* * * * *